United States Patent [19]

Bossen et al.

[11] Patent Number: 5,164,048

[45] Date of Patent: Nov. 17, 1992

[54] COOLING STRUCTURE FOR STABILIZING THE TEMPERATURE OF BEAMS IN A SHEET-MAKING APPARATUS

[75] Inventors: David A. Bossen, Palo Alto; Mathew G. Boissevain, Los Altos; Paul J. Houghton, Los Gatos, all of Calif.

[73] Assignee: Measurex Corporation, Cupertino, Calif.

[21] Appl. No.: 645,949

[22] Filed: Jan. 25, 1991

Related U.S. Application Data

[63] Continuation-in-part of Ser. No. 575,101, Aug. 29, 1990, abandoned.

[51] Int. Cl.$^5$ .......................... D21F 7/06; D21F 7/00; G01B 11/06; G01B 7/06
[52] U.S. Cl. ...................... 162/272; 73/159; 162/263
[58] Field of Search ................ 162/336, 263, 272; 73/159, 160

[56] References Cited

U.S. PATENT DOCUMENTS

| | | | |
|---|---|---|---|
| 3,468,756 | 9/1969 | Villa | 162/344 |
| 3,585,105 | 6/1971 | Stuebe | 162/352 |
| 3,766,386 | 8/1973 | Sivilotti et al. | 250/395 |
| 3,769,154 | 10/1973 | Wolf | 162/336 |
| 3,828,248 | 8/1974 | Wennerberg | 73/159 |
| 4,008,123 | 2/1977 | Kirjavainen | 162/336 |
| 4,455,197 | 6/1984 | Croteau et al. | 162/344 |
| 4,539,074 | 9/1985 | Stenberg | 162/347 |
| 4,552,619 | 11/1985 | Laitinen et al. | 162/336 |
| 4,692,213 | 9/1987 | Dove | 162/347 |
| 4,832,794 | 5/1989 | Lyytinen | 162/336 |

FOREIGN PATENT DOCUMENTS

| | | | |
|---|---|---|---|
| 0849817 | 8/1970 | Canada | 162/336 |
| 0065361 | 4/1982 | European Pat. Off. | |
| 0094669 | 5/1983 | European Pat. Off. | |
| 2529664 | 6/1983 | France | |
| 448544 | 12/1967 | Switzerland | |
| 1145229 | 3/1969 | United Kingdom | 162/336 |

OTHER PUBLICATIONS

R. M. Howard, "Recent Advances In Highspeed X-ray Thickness Gauging of Steel Strip":, ISA Transactions, vol. 9, No. 4, pp. 328–354 (1970).

Primary Examiner—William A. Cuchlinski, Jr.
Assistant Examiner—Diego F. F. Gutierrez
Attorney, Agent, or Firm—Spensley Horn Jubas & Lubitz

[57] ABSTRACT

Apparatus utilized in the continuous manufacture of sheet material, such as paper, includes a frame having at least one hollow beam for carrying means such as sheet-gauging heads operatively associated with the sheet material being fabricated. Thermal stability of the at least one hollow beam is enhanced by circulating fluid within the beam. Fluid displacement means which may be in the form of a series of inserts disposed end-to-end within the hollow beam define with the interior wall of the beam a fluid conduction channel. The fluid displacement means may also include generally helically oriented guides projecting into the fluid conduction channel for inducing turbulence in the circulating fluid.

5 Claims, 7 Drawing Sheets

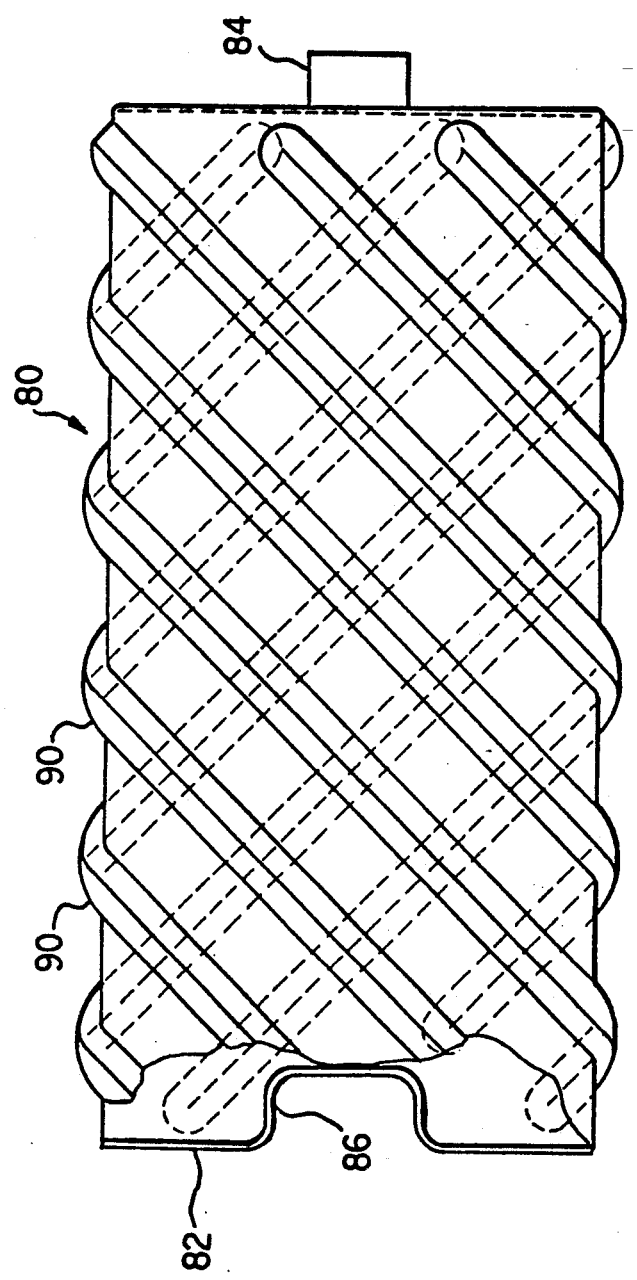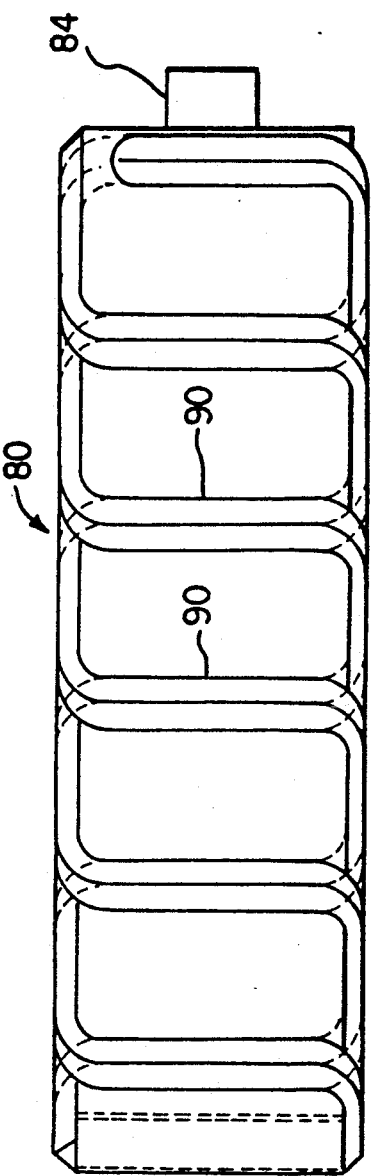

COOLING STRUCTURE FOR STABILIZING THE TEMPERATURE OF BEAMS IN A SHEET-MAKING APPARATUS

CROSS REFERENCE TO RELATED APPLICATION

This application is a continuation-in-part of application Ser. No. 575,101 filed Aug. 29, 1990 for "System and Process for Measuring Properties of a Moving Sheet of Material", now abandoned.

BACKGROUND OF THE INVENTION

A common industrial process is the manufacturing of continuous sheets of material, such as paper and plastic, and in order to control the production process sheet-gauging apparatus are used. For example, U.S. Pat. No. 3,621,259 owned by Measurex Corporation teaches a sheet gauging apparatus which includes two beams, one located above the sheet and one located below the sheet. Gauging head assemblies are mounted on the beams and the assemblies include sources and detectors. The sheet gauging apparatus also includes means to reciprocate the gauging head assemblies along tracks carried by the beams to allow measurement of various properties of the sheet at different positions on the sheet. For example, in a paper manufacturing process the moisture content, thickness, basis weight and many other properties of the paper sheet can be measured. It is common in practice for the sheet materials which are being measured by the gauging apparatus to sometimes be quite hot. Radiant heat from the sheet and steam rising from the sheet can cause temperature gradients in the beams which can result in deflection or deformation of the beams and tracks. The deflection or deformation results in variability of the separation of the gauging head assemblies as they travel along the tracks across the sheet which can cause measurement errors.

To reduce deflection and deformation of the beams and tracks, the system taught in U.S. Pat. No. 3,621,259 includes two fans to draw cool air from outside the device and to cause the air to flow longitudinally along the tracks and beams to stabilize the temperature thereof along their entire lengths. However, in some cases this system does not sufficiently reduce deflection of the beams.

Certain techniques are also known to compensate for the variability of the space between the gauging heads. For example, U.S. Pat. No. 4,678,915 owned by Measurex Corporation teaches a device for providing such compensation by determining the separation of the head assemblies and correcting the measured values of the parameter of interest (for example, basis weight, moisture content, and the like) according to the separation of the head assemblies. However, for certain measurements it is desirable to minimize the compensation which is required.

Accordingly, it is an overall object of the present invention to provide an improved system for reducing the thermal deflection and deformation of the beam and tracks in a sheet gauging apparatus.

SUMMARY OF THE INVENTION

In accordance with the broad aspects of the present invention, a sheet-gauging apparatus is provided for determining properties of a travelling sheet such as a paper web. The apparatus comprises a gauging head assembly adapted to scan the sheet and measure certain characteristics thereof. The properties to be determined are related to the measured characteristics. The gauging head assembly is carried by a support which defines a fluid-conducting channel. Means, such as a motor driven pump, causes fluid to flow in the channel, the flowing fluid reducing temperature gradients between different parts of the support to reduce deflection or deformation thereof.

In accordance with another aspect of the invention, inserts may be disposed within the support channel for defining a fluid conduction passage having a flow cross section substantially smaller than that of the channel. The inserts, which are disposed end-to-end within the channel, preferably include outer, spiral ridges projecting into the fluid conduction passage for inducing turbulence in the flowing fluid.

BRIEF DESCRIPTION OF THE DRAWINGS

Further objects, features and advantages of the invention will become apparent from the detailed description which follows when taken in conjunction with the accompanying drawings in which:

FIG. 4 is a side elevation view of one component of the present embodiment.

FIG. 5 is a plan view of the component shown in FIG. 4.

DESCRIPTION OF THE PREFERRED EMBODIMENT

Figure 1:
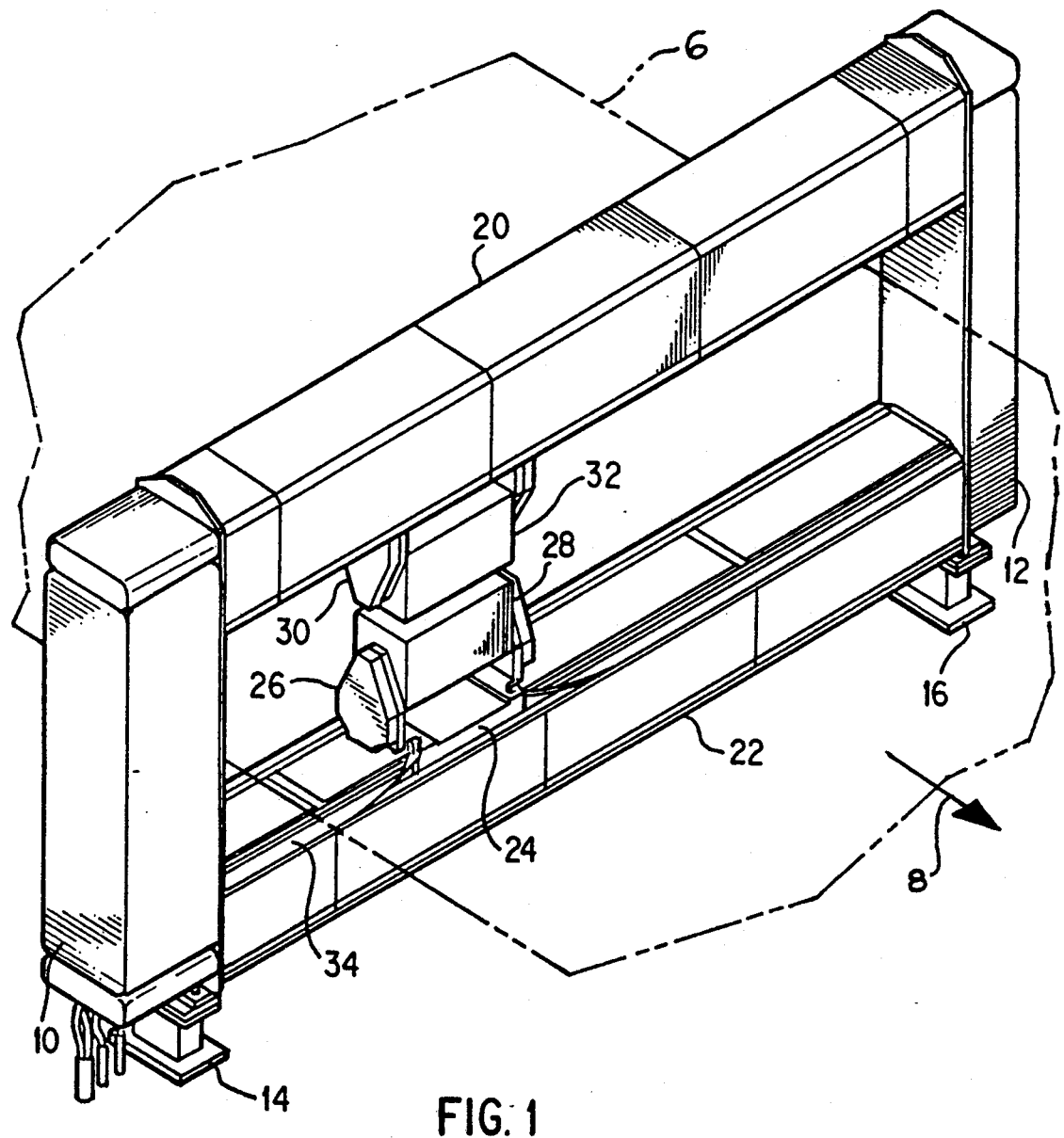
FIG. 1 is an isometric view of a sheet-gauging apparatus incorporating the present embodiment.

The preferred embodiment of the sheet-gauging apparatus is shown in FIG. 1. The embodiment shown in FIG. 1, designed to cooperate with sheet material 6 traveling through the apparatus in a direction denoted by an arrow 8, includes a left housing 10 and a right housing 12 which are vertically mounted on left base 14 and right base 16, respectively. In practice the bases 14 and 16 are mounted to a solid surface such as the floor of an industrial facility.

An upper, horizontal housing 20 is disposed between the left housing 10 and the right housing 12 and a lower, horizonal housing 22 is located between the housings 10 and 12 and is parallel to the upper housing 20 and vertically spaced apart therefrom. A lower carriage 24 is mounted on the lower housing 22, and similarly, an upper carriage, not shown, is connected to the bottom of the upper housing 20. Two lower head supports 26 are coupled one to either end of the lower carriage 24, and a lower head assembly 28 is mounted between the lower head supports 26. Similarly, there are two upper head supports 30 coupled to the upper carriage assembly, not shown, and upper head assembly 32 is connected between the upper head supports 30. Seals 34 are connected to the lower housing 22 and the upper housing 20. The seals 34 are flexible and help to prevent material from entering the interior of the housings 20 and 22.

Figure 2:
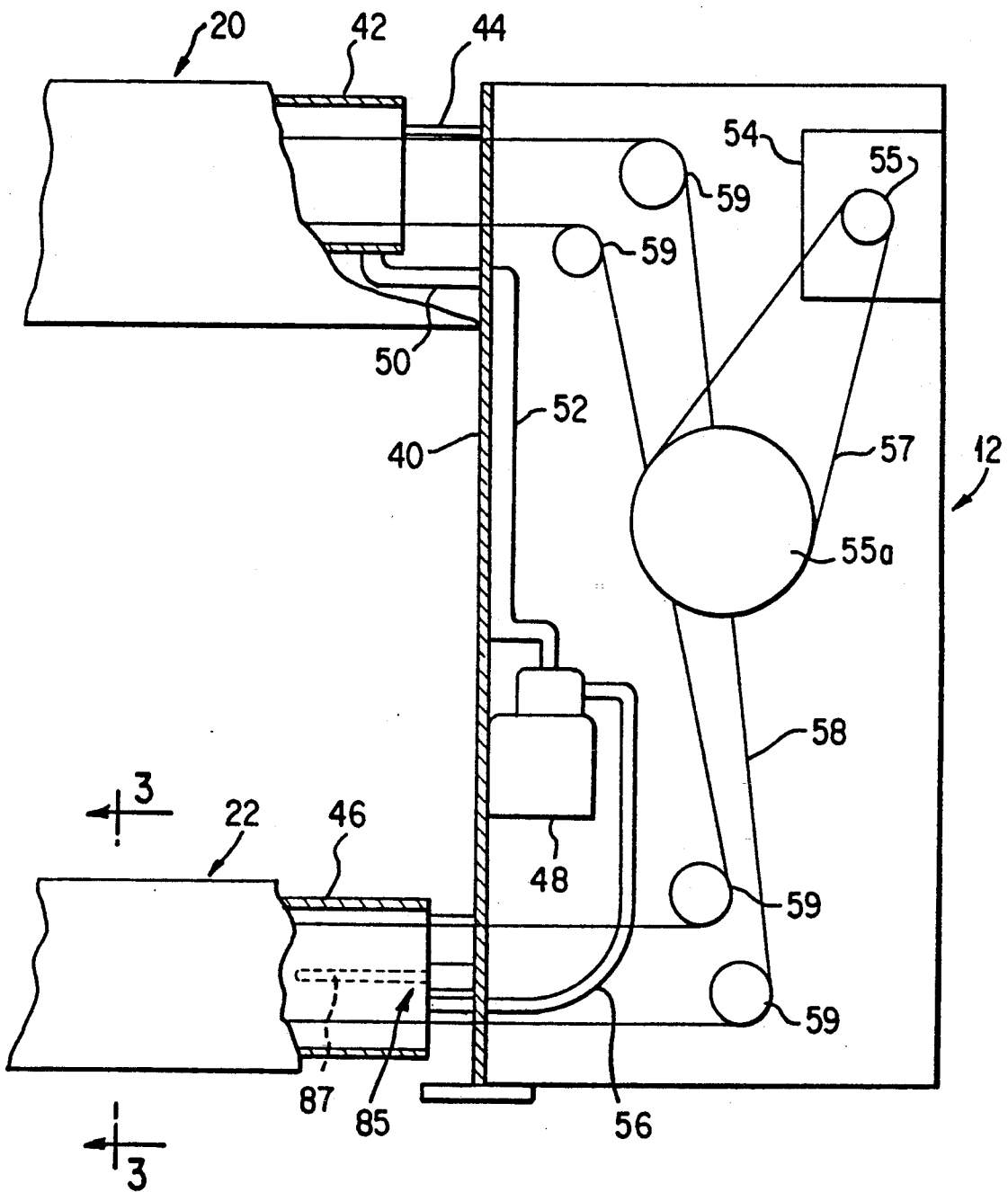
FIG. 2 is a from elevation view of one portion of the system shown in FIG. 1 with part of the housing broken away and portions thereof shown in cross section.

FIG. 2 shows the right hand ends of the upper and lower housings 20 and 22 and components of the device located within the interior of the right housing 12. Part of the housing 12 has been cut away to show interior components, and similarly the right ends of housings 20 and 22 have been broken away to show components located inside. A vertical support 40 is located within the right housing 12, and the vertical support 40 is a rectangular plate mounted on the right base 16. An upper, horizontal support 42 is coupled to the top end of the vertical support 40 by connecting bracket 44, and similarly a lower, horizontal support 46 is coupled by a connecting bracket to the lower end of the vertical support 40. The upper support 42 and lower support 46 extend substantially horizontally between the vertical support 40 at the right end of the device and another vertical support, not shown, which is located in the left housing 10. The horizontal supports 42 and 46 and vertical support 40 and the vertical support located inside housing 10 together form a frame.

A pump and motor assembly 48 is connected to the vertical support 40, and a conduit 50 is connected to lower side of the upper support 42 to provide fluid communication between the interior of the upper support 42 and a pipe 52 which is mounted on the vertical support 40. The pipe 52 is mounted in contact with the vertical support 40 to provide thermal communication between fluid within the pipe 52 and the vertical support 40. The lower end of pipe 52 is connected to the pump and motor assembly 48. Pipe 56 is connected to the pump and motor assembly 48 to carry fluid therefrom into the interior of the lower support 46.

Enclosed in the housing 12 is a drive means to cause the carriages, not shown, to travel back and forth along tracks 66 (seen in FIG. 3) mounted on the supports 42 and 46. The drive means includes a motor 54 mounted on to the inside of housing 12, and a drive sprocket 55 on the motor 54. A belt 57 travels around the sprocket 55 and around driven sprocket 55a which drives another belt 58. The belt 58 travels around idle rollers 59, and the lower part of belt 58 travels through the lower housing 22 and is connected to the lower carriage 24. The belt 59 travels around a similar set of rollers located in the left housing 10. Accordingly, the motor is operable to drive the lower carriage 24 in a reciprocating fashion along the lower support 46. Similarly, the motor simultaneously drives the upper carriage along the upper support 42 in unison with the lower carriage 24.

Figure 3:
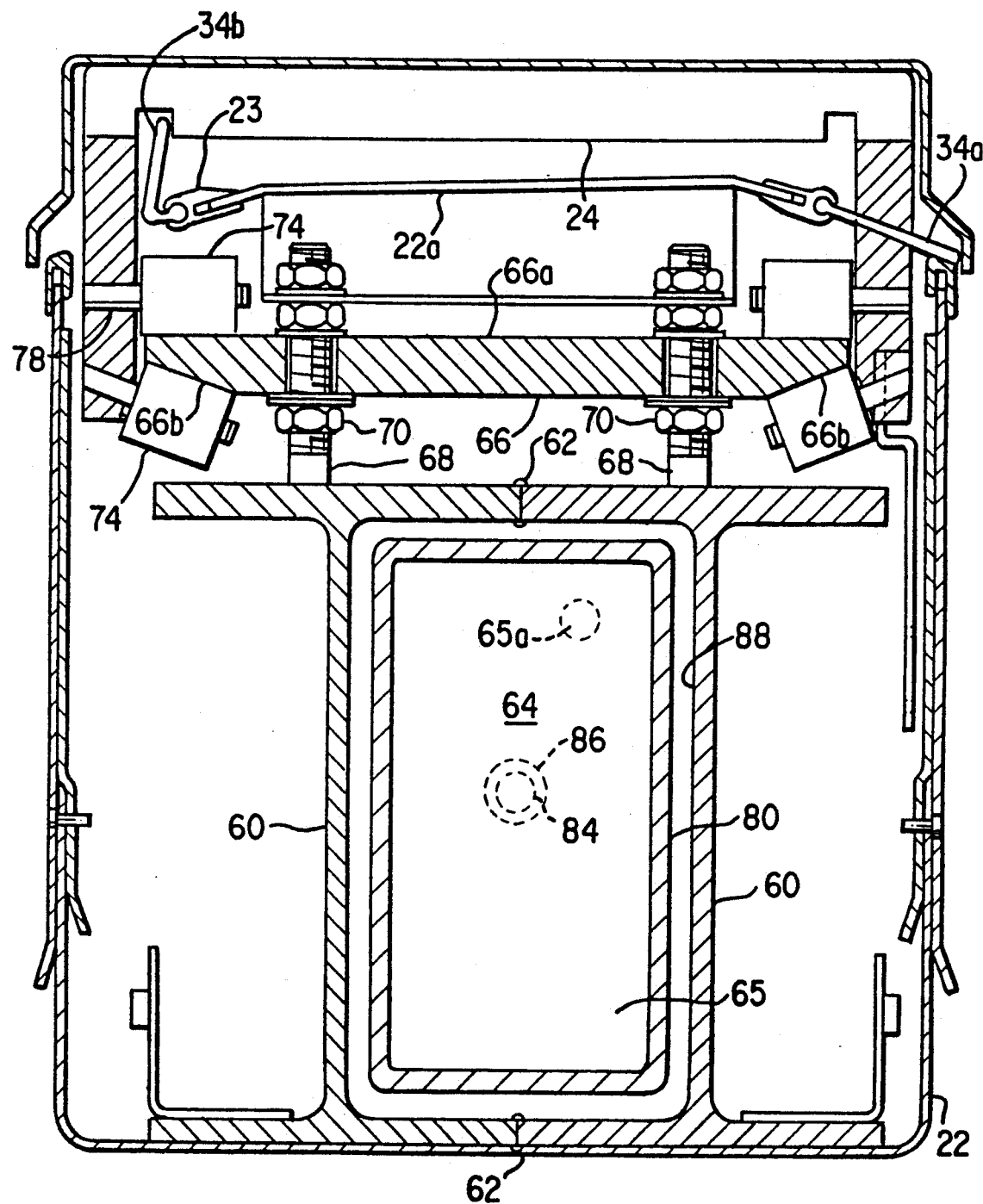
FIG. 3 is a cross section view taken along line 3—3 of FIG. 2.

Turning now to FIG. 3, there is shown a section of the lower housing 22 and lower support 46 taken along line 3—3 in FIG. 2. As shown in FIG. 3, the lower support 46 includes two I beams 60 which are welded together at seams 62. The seams 62 are continuous along the length of the I beams so that a water tight channel 64 is formed between the two I beams 60. A horizontal track 66, parallel with and spaced apart from the I beams 60, is secured to the beams 60 by studs 68 and nuts 70. The track 66 has a flat upper surface 66a while the lower surface thereof has tapered end portions 66b. The lower part of the lower carriage 24 is shown in FIG. 3, but for clarity the upper portions of the lower carriage 24 are not shown. The lower carriage 24 has two arms 72 which depend from either side thereof and extend adjacent the outer edges of the track 66. Two wheels 74 are mounted on the lower part of each arm 72 by axles 78. The wheels 74 are located and oriented so that they snugly engage the outer end portions of the upper surface 66a and the tapered end portions 66b of the lower surface of the track 66. Accordingly, the lower carriage 24 can travel smoothly along track 66 in alignment therewith. As the lower carriage 24 travels, the seals 34 are forced upward to accommodate the arms 72, and after the carriage 24 passes, the seals 34 resume the position shown in FIG. 3. The interior edges of seals 34 are coupled to the upper members 22a of the housing 22 by connectors 23, throughout the length of the housing 22. The exterior edges of seals 34 are free to move up and down so that normally the seals 34 are in the position indicated as 34a to prevent dirt from entering the housing 22, and when the carriage 24 is adjacent a particular portion of the seals, that portion is deformed into the position indicated as 34b. Rollers, not shown, are provided on the carriage 24 to urge the seals into positions 34a and 34b.

The ends of channel 64 are sealed by plates, such as the plate 65. A port 65a is formed in the plate 65 at the end of the lower support 46 located adjacent the left housing 10 to permit fluid to exit from the channel 64 and flow through a pipe, not shown, which is connected to a similar port in the upper support 42.

It should be understood that upper support 42 is substantially identical to the lower support 46, except that the upper support 42 is inverted relative to the orientation of support 46.

Turning to FIGS. 4 and 5 there is shown fluid displacement and turbulence means. The fluid displacement and turbulence means includes an insert or hollow member 80 which has thin walls 82. A screw-on cap 84 is connected to one end of the hollow member 80 by means of threaded connection, not shown. A corresponding indentation 86 is formed in the end of the hollow member 80 opposite the cap 84, and the indentation 86 is sized slightly larger than the cap 84. A plurality of ridges 90 are formed on the outer surface of the hollow member 80, and the ridges form a generally spiral pattern along the length of the exterior of the hollow member 80.

With reference to FIG. 3, a plurality of inserts or hollow members 80 are inserted end to end in the channel 64. The cap 84 of each hollow member 80 fits within the corresponding indentation 86 of the adjacent hollow member 80. The hollow members 80 and their ridges 90 are so dimensioned and located that when the members 80 are within the channel 64 the outer edges of the ridges 90 contact the internal surfaces of the I beams 60. The internal surfaces of the beams 60, the inserts 80 and the ridges 90 thereby define a spiral fluid conduction passage 88, substantially smaller in cross section than the channel 64, throughout the length of the support 46. Likewise, a series of inserts 80 are inserted in the corresponding channel in the upper support 42 to form a spiral passage similar to the passage 88 in the channel 64 of the lower support 46.

The liquid conduction system including passage 88, the corresponding passage in the upper support 42, and the pump and piping, is filled, in accordance with one form of the invention, with a mixture of water and automobile-type antifreeze. The pump and motor assembly 48 continuously circulates the mixture through the supports 42 and 46.

It is common in practice that sheet materials being measured by the gauging apparatus can be quite hot. Hot vapor such as steam sometimes rises from the sheet and radiant heat from the sheet can also affect the supports. Moreover, interruptions in the production of the sheet can result in temporary cooling of the supports. Hot vapor and radiant energy from the sheet tends to heat the lower portions of the upper support 42 substantially more than the upper portions thereof. Similarly, those portions of the lower support 46 which are nearest the sheet are more affected than portions which are further away. Temperature gradients in the supports can result in significant deflection and/or deformation of the supports. However, we have found that in the present embodiment the temperature gradients in the supports are substantially reduced since heat is transferred from the relatively hotter portions of the supports to the flowing fluid and thereafter to cooler portions of the supports. Accordingly, deflection and deformation of the supports is reduced. Without the present invention, thermal gradients can also occur in the vertical supports 40 and cause deflection and deformation of the gauging apparatus, and such gradients are reduced by the present invention.

We have found that the ridges 90 on the hollow members 80 create sufficient turbulence in the fluid to enhance the heat transfer capability of the system and thereby reduce thermal gradients between portions of the supports 42 and 46. We have also found that the hollow members 80 provide added advantages. In practice, we have found it desirable to seal the fluid contained in the system consisting of the supports 42 and 46 and the pump and piping 40, 50 and 52. When the system is sealed air cannot mix with the fluid and corrosion of the I beams is thereby reduced. However, if the hollow members 80 were not used, sealing the system would not be practical because of thermal expansion and contraction of the fluid due to the wide temperature variations experienced by the system. But since the hollow interiors of members 80 are filled with air, they expand and contract as necessary to accommodate thermal expansion and contraction of the fluid. Another advantage of the hollow members 80 is that their use results in a significant reduction in the amount of fluid which is necessary since only the spiral passage 88 contains fluid. The amount of fluid is, of course, substantially less than what would be required if the channels 64 were completely filled.

Optionally, the system can include means to heat the liquid inside the channel 64. With reference to FIG. 2, the heating means includes an electrically powered heater 85 which is mounted on the vertical support 40 and has a resistive heating element 87 which extends a short distance into the channel 64. In certain cases the heater 85 may be used to keep the upper and lower supports 42 and 46 above ambient temperature. For example, when the sheet-making process is temporarily suspended, it may be useful to operate the heater 85 and the pump 48 to keep the supports 42 and 46 at about the temperature they would be when the sheet making process is operating. Thus, when production is resumed the supports will not be heated and undergo deformation. Also, the heater 85 may be used to keep the supports above the dew point temperature thereby preventing condensation of water on the supports, which could result in water droplets falling on the sheet.

Although in the system shown in FIG. 1 the upper housing 20 and the lower housing 22 are substantially horizontal, it should be understood that the present invention is also applicable to sheet-making processes wherein the sheet and/or housings 20 and 22 are disposed vertically or at some other angle.

It should also be understood that the preferred embodiment is described herein as applied to a device which is sometimes called an "O-frame" scanner due to the shape defined by the housings. Other types of scanners are also sometimes used, and the present invention is equally applicable to those other types as well. For example, in addition to the conventional "O-frame" scanner there is also a design called a "C-frame" scanner which is similar to the "O-frame" scanner except that it has only one end housing. The carriages and head assemblies in a "C-frame" scanner do not move relative to the upper and lower supports 40 and 42. Rather, in a "C-frame" scanner the head assemblies are fixed relative to the support members, and the support members along with the head assemblies are driven to reciprocate back and forth across the sheet. A C-frame scanner is taught for example, in U.S. Pat. No. 3,840,302.

Figure 6:
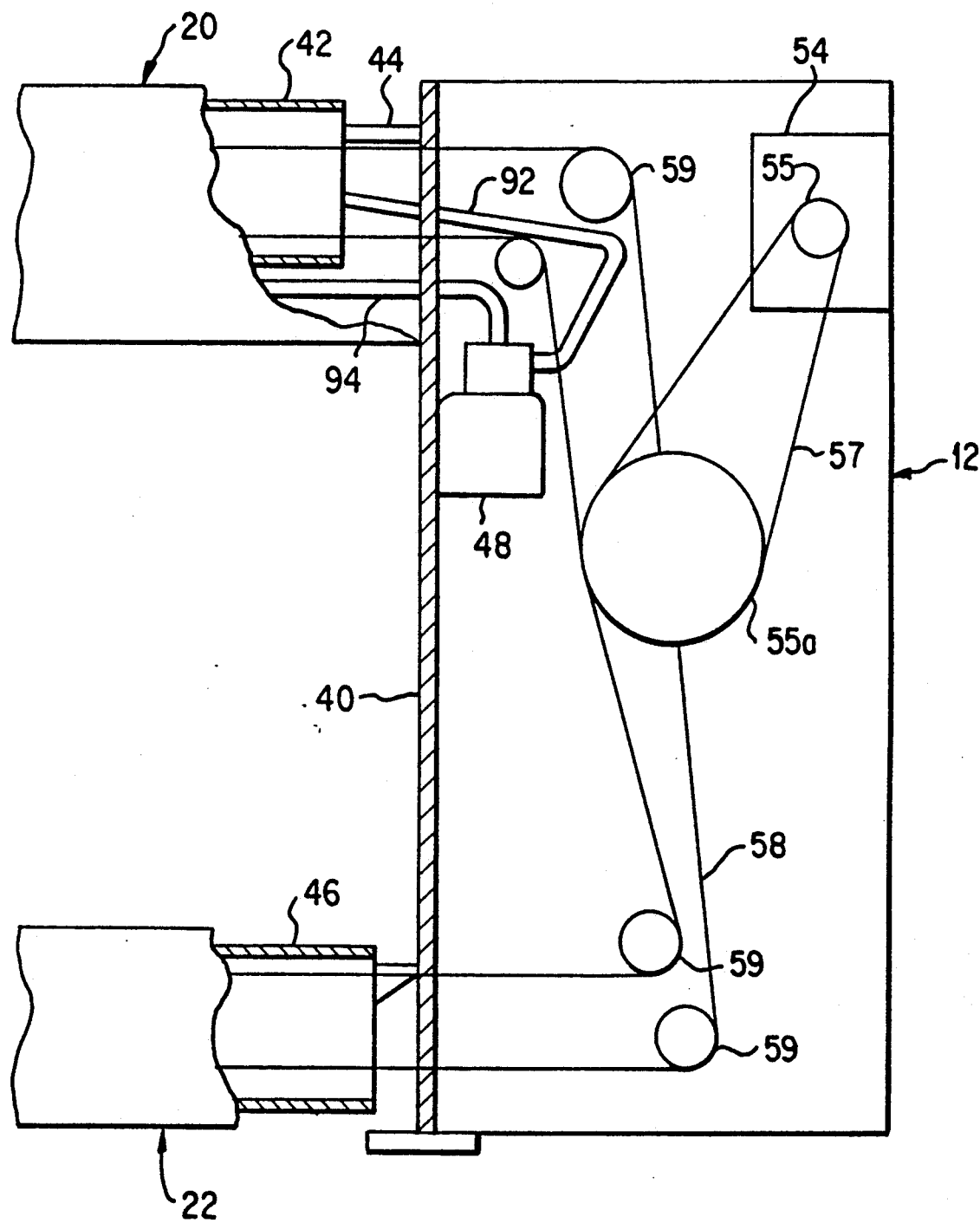
FIG. 6 is a front elevation view, like that of FIG. 2, showing an alternative embodiment of the present invention.

In some circumstances it may be necessary to circulate liquid only in one of the supports 42 or 46. FIG. 6 illustrates such an alternative embodiment, in which the pump and motor assembly 48 is connected by a pipe 92 to receive fluid from the right end of support 42. Liquid from the pump 48 flows through a pipe 94 located inside the housing 20 to the left end of the support 42 where it enters the support 42 to flow through the channel inside support 42.

It should be noted that the track 66 is normally made of fiberglass and that liquid is not circulated through the track. This can result in differences in thermal expansion and contraction between track 66 and the support 42 or 46 to which it is attached.

In some scanner systems, particularly longer ones, we have found that this can cause undesirable deformation of the track 66 since the tracks are bolted to the supports. However, any such problems can be overcome by the system shown in FIGS. 7-10.

Figure 7:
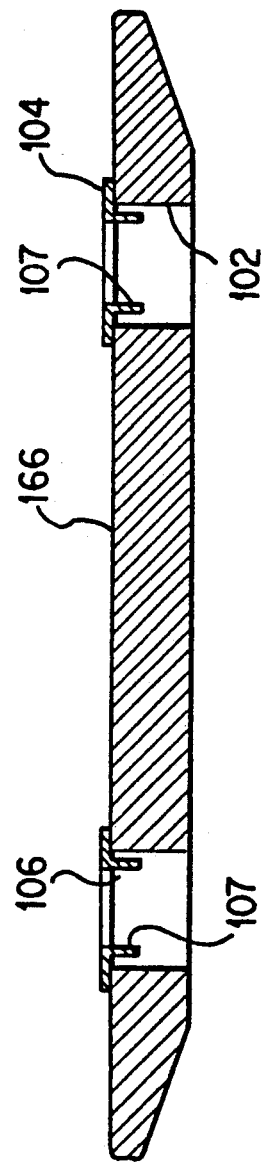
FIG. 7 is a side elevation view, in cross section, of an alternative embodiment of a track which may be used in the system of the present invention.
Figure 9:
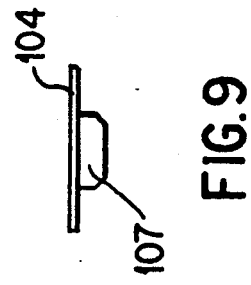
FIGS. 8 and 9 are details of a component used in connection with the track of FIG. 7.

FIG. 7 shows a cross section of an alternative track 166 having a plurality of holes 102 for attachment to the studs 68. The holes 102 are somewhat larger than the studs 68, and metal brackets 104 are fitted into the holes 102. Each metal bracket 104, one of which is shown in detail in FIGS. 8 and 9, has a hole 106 which is generally rectangular. The long sides of the hole 106 have depending tabs 107. The brackets 104 are pressed into the fiberglass track 166 so that they are permanently attached to the track 166 with the long dimension of the hole 102, and the tabs 107, oriented along the length of the track 166.

Figure 8:
Figure 10:
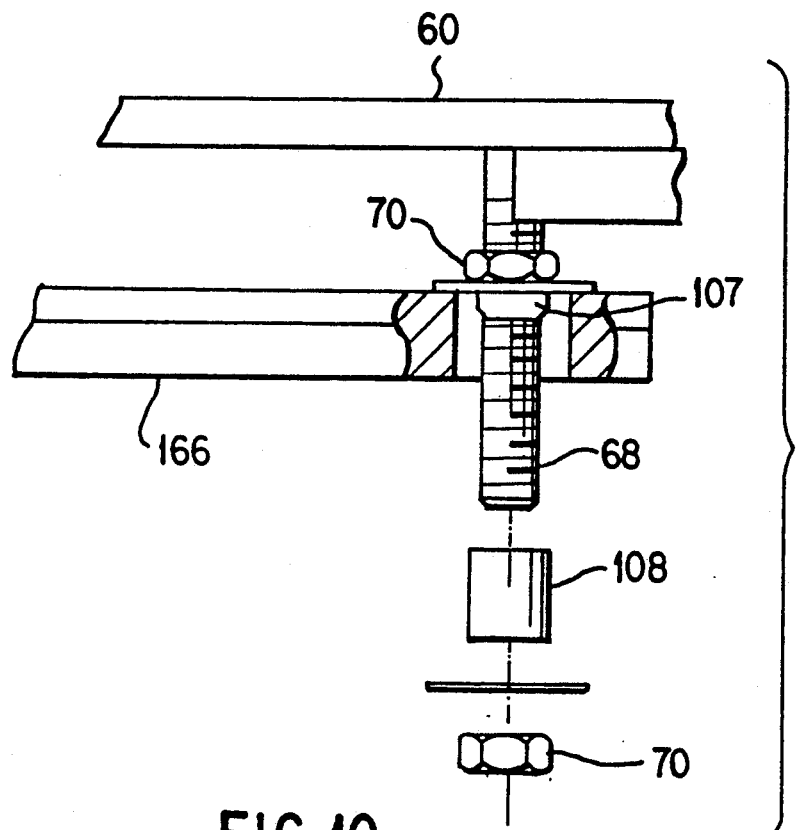
FIGS. 10 and 11 are front and side elevation views, respectively, partly in cross section, of the alternative embodiment of FIGS. 7-9.
Figure 11:
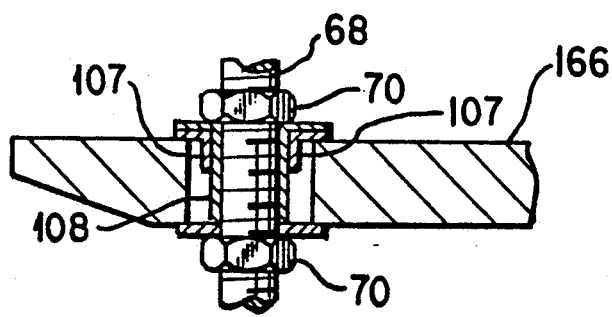

When the track 166 is assembled to the studs 68, a bushing 108 is located around each stud as shown in FIGS. 10 and 11. (FIG. 10 shows the track 166 in the upper housing 20.) The outside diameter of the bushing is the same as the short dimension of the hole 106, while the long dimension of the hole 106 is, of course, longer than the diameter of the bushing. (FIG. 8.) The length of the bushing is slightly greater than the thickness of the track 166. Accordingly, when the nuts 70 are tightened against the bushings 108 and washers 109 the track 166 can move relative to the studs and the I beams 60 in the dimension parallel to the length of the track 166, but the track 166 cannot move relative to the beams 60 in the other two dimensions. Accordingly, when the beams 60 and the track 166 expand or contract relative to one another, they move relative to one another only in the dimension along the track so that the track 166 is not deformed.

What is claimed is:

1. In an apparatus for the continuous manufacture of sheet material having a direction of travel through said apparatus, a combination including:
   a frame including at least one hollow beam extending transversely of the direction of travel of said sheet material and carrying means operatively associated with said sheet material, said at least one hollow beam having an interior wall;
   a series of inserts disposed end to end within said at least one beam for defining with said interior wall a fluid conduction channel extending about said inserts; and
   means for circulating fluid through said fluid conduction channel, whereby the temperature of said at least one beam is stabilized.

2. The combination set forth in claim 1 in which said inserts comprise thin-walled, hollow structures expandable and contractible to accommodate thermal expansion and contraction of the circulating fluid.

3. The combination set forth in claim 11 in which said inserts include generally helically oriented guides projecting into the fluid conduction channel for inducing turbulence in the circulating fluid.

4. The combination set forth in claim 1 including means in heat transfer relationship with the circulating fluid for heating the circulating fluid.

5. The combination set forth in claim 1 in which the flow cross section of the fluid conducting channel is substantially smaller than the cross section of the interior of said at least one beam.

* * * * *